United States Patent [19]

Moon

[11] 4,335,140
[45] Jun. 15, 1982

[54] INSECTICIDAL TRIFLUOROETHANIMIDOTHIOATE DISULFIDES

[75] Inventor: Marcus P. Moon, Wilmington, Del.

[73] Assignee: E. I. Du Pont de Nemours and Company, Wilmington, Del.

[21] Appl. No.: 232,565

[22] Filed: Feb. 9, 1981

[51] Int. Cl.$^3$ .................... A01N 37/06; C07C 119/20
[52] U.S. Cl. ................................ 424/298; 260/453.1
[58] Field of Search ..................... 260/453.1; 424/298

[56] References Cited

U.S. PATENT DOCUMENTS

| | | | |
|---|---|---|---|
| 3,318,681 | 5/1967 | Yates | 260/453.1 |
| 4,080,469 | 3/1978 | D'Silva | 260/453 |
| 4,081,550 | 3/1978 | D'Silva | 424/298 |
| 4,138,423 | 2/1979 | D'Silva | 260/453 |
| 4,179,514 | 12/1979 | D'Silva | 424/277 |

*Primary Examiner*—John M. Ford
*Assistant Examiner*—Robert C. Whittenbaugh

[57] ABSTRACT

Trifluoroethanimidothioate disulfides, such as methyl 2,2,2-trifluoro-N-[N-methyl-N-[[2-(propoxy-carbonyl)-phenyl]dithio]aminocarbonyloxy]ethanimidothioate, are useful for control of insects.

37 Claims, No Drawings

INSECTICIDAL TRIFLUOROETHANIMIDOTHIOATE DISULFIDES

BACKGROUND OF THE INVENTION

This invention relates to insecticidal trifluoroethanimidothioate disulfides.

U.S. Pat. No. 4,179,514, U.S. Pat. No. 4,080,469, U.S. Pat. No. 4,081,550 and U.S. Pat. No. 4,138,423 disclose various pesticidal compounds of divergent structures.

SUMMARY OF THE INVENTION

This invention pertains to novel compounds of structure I, their agriculturally useful compositions, and their method of use as insecticides.

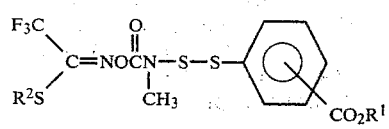

wherein $R^2$ is $C_1$–$C_4$ alkyl, $C_3$–$C_4$ alkenyl, or benzyl; and
$R^1$ is $C_1$–$C_{20}$ alkyl or $C_5$–$C_8$ cycloalkyl.

Preferred for their high level of activity and/or ease of synthesis are those compounds of structure I wherein $R^2$ is $CH_3$ or $R^1$ is $C_1$–$C_8$ alkyl.

More preferred for their higher activity and/or greater ease of synthesis are those preferred compounds wherein the $CO_2R^1$ group is in the ortho position.

Most preferred for their highest activity and/or greatest ease of synthesis are those more preferred compounds wherein $R^1$ is $C_1$–$C_8$ alkyl.

Specifically preferred for their excellent activity and/or excellent ease of synthesis are:

Methyl 2,2,2-trifluoro-N-[N-methyl-N-[[2-(propoxycarbonyl)phenyl]dithio]aminocarbonyloxy]ethanimidothioate;

Methyl 2,2,2-trifluoro-N-[N-[[2-(3-methylbutoxycarbonyl)phenyl]dithio]-N-methylaminocarbonyloxy]ethanimidothioate;

Methyl 2,2,2-trifluoro-N-[N-[[2-(methoxycarbonyl)phenyl]dithio]-N-methylaminocarbonyloxy]ethanimidothioate;

Methyl 2,2,2-trifluoro-N-[N-[[2-(1-methylethoxycarbonyl)phenyl]dithio]-N-methylaminocarbonyloxy]ethanimidothioate;

Methyl 2,2,2-trifluoro-N-[N-[[2-(ethoxycarbonyl)phenyl]dithio]-N-methylaminocarbonyloxy]ethanimidothioate; and Methyl 2,2,2-trifluoro-N-[N-[[2-(butoxycarbonyl)phenyl]dithio]-N-methylaminocarbonyloxy]ethanimidothioate.

This application also pertains to the novel process for preparing the disulfides (I) from a carbamoyl fluoride (II) and a mercaptobenzoic acid ester (III) as shown in Equation A, wherein $R^1$ and $R^2$ are defined Equation A

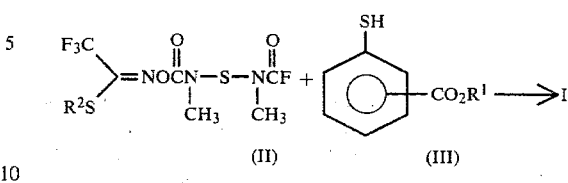

as above.

SYNTHESIS

Compounds of Formula I are prepared by the reaction of carbamoyl fluoride (II) with a mercaptobenzoic acid ester (III) via a phase transfer process at ambient temperature and atmospheric pressure using aqueous base, a suitable organic solvent (e.g., $CH_2Cl_2$, $CHCl_3$, $CCl_4$, or benzene), and a tetraalkyl ammonium halide as a phase transfer catalyst. In the above reaction, a solution of II and the catalyst in the chosen solvent is vigorously stirred as an equimolar amount of aqueous base and an excess of III dissolved in the chosen solvent are simultaneously added. The resulting mixture is stirred for up to 24 hours but is generally complete within 5 hours. The two phase mixture is separated and the organic phase is washed with water, dried with $MgSO_4$, filtered, and concentrated in vacuo. The resulting compound I is purified by methods known to those skilled in the art, such as, recrystallization, column chromatography, or another suitable procedure.

Carbamoyl fluorides II can be prepared, as shown in Equation B, by reacting oximes IV with biscarbamoyl fluoride V in the presence of an acid acceptor at Equation B

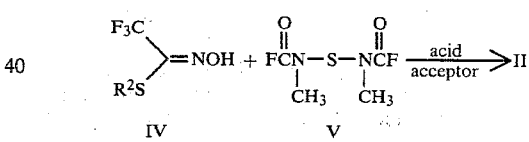

temperatures between $-25°$ C. and $50°$ C. This reaction can be carried out in solvents such as benzene, toluene, methylene chloride, chloroform, ethylene dichloride, acetone, tetrahydrofuran, acetonitrile, or water. Mixtures of these solvents may be used. Suitable acid acceptors include, but are not limited to, triethylamine, pyridine, and NaOH.

Oximes IV can be prepared by the synthetic route outlined in Scheme A. The diacylhydroxylamine VI is heated with $PCl_5$ Scheme A

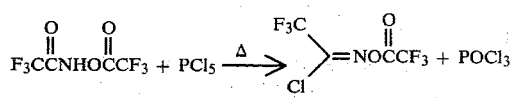

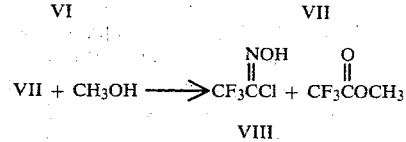

-continued
Scheme A

to afford o-(trifluoroacetyl)acetohydroxamoyl chloride VII which upon treatment with a suitable alcohol, such as methanol, give acetohydroxamoyl chloride VIII. Reaction of the sodium salt of thiols ($R^2SNa$) with VIII affords intermediate oximes IV.

The synthesis of mercaptobenzoic acid esters III is described by P. F. Wiley [J. Org. Chem. 16, 810 (1951)].

The preparation of biscarbamoyl fluoride V from N-methylcarbamoyl fluoride and sulfur dichloride is described in Belgian BE 848,913.

Diacylhydroxylamine VI can be prepared from trifluoroacetic anhydride and hydroxylamine hydrochloride by methods known to those skilled in the art.

In the following examples, temperatures are in degrees centigrade.

EXAMPLE I

Methyl 2,2,2-trifluoro-N-[N-[[2-(1-methylethoxycarbonyl)-phenyl]dithio]-N-methylaminocarbonyloxy]ethanimidothioate 2-Propyl thiosalicylate (2 g) dissolved in 10 ml $CH_2Cl_2$ and 1 N NaOH (10 ml) were slowly and simultaneously added to a vigorously stirred $CH_2Cl_2$ (50 ml) solution of II($R^2=CH_3$) (3.2 g) and a catalytic amount of tetrabutyl ammonium chloride. After 5 hours, the aqueous layer was removed and the $CH_2Cl_2$ layer was washed with water, dried with $MgSO_4$, filtered, and concentrated in vacuo to a crude oil which was chromatographed on silica (10% hexane:90% $CH_2Cl_2$) to afford 1.6 g of methyl 2,2,2-trifluoro-N-[N-[[2-(1-methylethoxycarbonyl)phenyl]dithio]-N-methylaminocarbonyloxy]ethanimidothioate as a clear yellow oil. $n_D$ 1.5560 ir (neat) $v1700$ (c=o) and 1760 (c=o). $^1H$ NMR (CDClhd 3)δ: 1.38, (d, 6H, $CH_3$), 2.60 (m, 3H, $SCH_3$), 3.28 (s, 3H, $NCH_3$), 5.27 (m, 1H, CH), and 7.17–8.42 (m, 4H, arom).

II($R^2=CH_3$) and the intermediates required for its preparation can be prepared as follows:

A. O-(Trifluoroacetyl)trifluoroacetohydroxamoyl Chloride

A mixture of 373 g (1.65 mol) of N,O-bis(trifluoroacetyl)hydroxylamine and 373 g of phosphorous pentachloride was warmed gently under an efficient reflux condenser until evolution of HCl gas stopped and the reaction mixture became a homogeneous liquid. Distillation gave 200.0 g (50%) of O-(trifluoroacetyl)trifluoroacetohydroxamoyl chloride as a colorless liquid: bp 84°–86°; $n_D^{25}$ 1.3272; ir (liquid) 6.12μ (C=N) and 5.41μ (C=O); $^{19}F$ NMR $(CFCl_3)δ$ −70.0 ppm (s) and −74.1 ppm (s).

Anal. Calcd. for $C_4ClF_6NO_2$: C, 19.73; Cl, 14.56; F, 46.82; N, 5.75. Found: C, 19.50; Cl, 14.87; F, 46.68; N, 5.87.

B. Trifluoroacetohydroxamoyl Chloride

Methanol, 21.0 g (0.065 mol) was added dropwise to 153 g (0.063 mol) of O-(trifluoroacetyl)trifluoroacetohydroxamoyl chloride cooled to 0°. The reaction mixture was allowed to warm to 25° and then distilled to give methyl trifluoroacetate, bp 44°, and then 84.8 g (91%) of trifluoroacetohydroxamoyl chloride as a colorless liquid: bp 90°–91°; ir (liquid) 6.11μ (C=N); $^{19}F$ NMR $(CFCl_3)δ$ −70.1 ppm (s).

Anal. Calcd. for $C_2HClF_3NO$: C, 16.28; H, 0.69; Cl, 24.04; F, 38.64; N, 9.50. Found: C, 16.38; H, 0.98; Cl, 24.18; F, 38.77; N, 9.51.

C. S-Methyl 2,2,2-Trifluoro-N-(methylcarbamoyloxy)thioacetamidate

Methanethiol, 38 ml (measured at 0°, 0.68 mol) was distilled into a solution prepared by dissolving 14.7 g (0.638 g atom) of sodium in 260 ml of methanol. The resulting solution was cooled to 0°, and 94.1 g (0.638 mol) of trifluoroacetohydroxyamoyl chloride was added dropwise, keeping the temperature below 10°. The reaction mixture was stirred at room temperature for 3 days, filtered to remove NaCl, and evaporated to dryness under reduced pressure. (Care should be taken to avoid loss of product due to sublimation). The residue was sublimed at 50°–60° and 0.5 mm pressure to give 84.71 g (83%) of S-methyl 2,2,2-trifluoro-N-(methylcarbamoyloxy)thioacetamidate as large, colorless crystals, m.p. 52°–54°. A sample prepared in a similar way was analyzed: ir (KBr) 3.05μ (OH) and 6.22μ (C=N); $^1H$ NMR $(CDCl_3)δ$ 2.53 ppm (m, 3H), 8.07 ppm (s, 1H); $^{19}F$ NMR $(CDCl_3)δ$ −66.6 ppm (q, $J=1$ Hz).

Anal. Calcd. for $C_3H_4F_3NOS$: C, 22.64; H, 2.53; F, 35.82; N, 8.80; S, 20.15. Found: C, 22.65; H, 2.40; F, 35.73; N, 8.85; S, 20.47.

D. Methyl (Z)-2,2,2-trifluoro-N-[[N-(fluorocarbonyl)-N-methylaminothio]-N-methylaminocarbonyloxy]ethanimidothioate A solution of 23.9 g (0.15 mol) of S-methyl (Z)-2,2,2-trifluoro-N-hydroxythioacetimidate in $CH_2Cl_2$ (made up to 160 ml) in one addition funnel and 160 ml (0.16 mol) of 1 N aqueous NaOH in a separate addition funnel were added simultaneously at the same rate over a period of 1 hour to a vigorously stirred solution of 28.74 g (0.16 mol) of N,N'-thiobis[N-methylcarbamoylfluoride] in 500 ml of methylene chloride at 25° in a 2-1 creased flask. After the addition, the reaction mixture was stirred for 1 hour, and then the organic layer was separated, washed with water, dried ($MgSO_4$), and evaporated to dryness under reduced pressure (1 mm Hg). There was obtained 43.16 g (89% yield) of methyl (Z)-2,2,2-trifluoro-N-[[(N-fluorocarbonyl)-N-methylaminothio]-N-methylaminocarbonyloxy]ethanimidothioate as a white solid, m.p. 55°–64°.

By the example provided, the following compounds can be made.

TABLE I

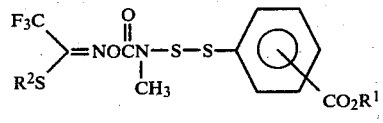

| Carboalkoxy Position | $R^1$ | $R^2$ | Physical Data |
|---|---|---|---|
| 2 | —$CH_3$ | —$CH_3$ | $n_D$ 1.5688 |
| 2 | —$C_2H_5$ | —$CH_3$ | $n_D$ 1.5649 |
| 2 | —$CH_2CH_2CH_3$ | —$CH_3$ | $n_D$ 1.5570 |
| 2 | —$CH(CH_3)_2$ | —$CH_3$ | $n_D$ 1.5560 |
| 2 | —$CH_2CH_2CH_2CH_3$ | —$CH_3$ | $n_D$ |
| 2 | —$CH_2CH_2CH(CH_3)_2$ | —$CH_3$ | $n_D$ 1.5516 |
| 2 | —$CH_2(CH_2)_4CH_3$ | —$CH_3$ | |
| 2 | —⟨S⟩ | —$CH_3$ | |

TABLE I-continued

| Carbo-alkoxy Position | R¹ | R² | Physical Data |
|---|---|---|---|
| 2 | $-CH_2(CH_2)_7CH_3$ | $-CH_3$ | |
| 2 | $-CH_2(CH_2)_{10}CH_3$ | $-CH_3$ | |
| 2 | $-CH_2(CH_2)_{18}CH_3$ | $-CH_3$ | |
| 3 | $-CH_3$ | $-CH_3$ | |
| 3 | $-CH_2(CH_2)_2CH_3$ | $-CH_3$ | |
| 4 | $-C_2H_5$ | $-CH_3$ | |
| 4 | $-CH_2(CH_2)_2CH_3$ | $-CH_3$ | |
| 2 | $-CH_3$ | $-CH_2CH_2CH_2CH_3$ | |
| 2 | $-CH_2CH_2CH_3$ | $-CH_2CH_2CH_2CH_3$ | |
| 3 | $-CH_2CH_3$ | $-CH_2CH_2CH_2CH_3$ | |
| 3 | $-CH(CH_3)_2$ | $-CH_2CH_2CH_2CH_3$ | |
| 4 | $-CH_3$ | $-CH_2CH_2CH_2CH_3$ | |
| 4 | $-CH_2(CH_2)_2CH_3$ | $-CH_2CH_2CH_2CH_3$ | |
| 2 | $-CH_3$ | $-CH_2CH=CH_2$ | |
| 2 | $-C_2H_5$ | $-CH_2CH=CH_2$ | |
| 3 | $-CH_3$ | $-CH_2CH=CH_2$ | |
| 3 | $-CH_2CH_2CH_3$ | $-CH_2CH=CH_2$ | |
| 4 | $-C_2H_5$ | $-CH_2CH=CH_2$ | |
| 4 | $-CH_3CHCH_3$ | $-CH_2CH=CH_2$ | |
| 2 | $-CH_3$ |  |  |
| 2 | $-CH_2CH_2CH_3$ |  |  |
| 3 | $-C_2H_5$ |  |  |
| 3 | $-CH_2CH_2CH_3$ |  |  |
| 4 | $-C_2H_5$ |  |  |
| 4 | $-CH(CH_3)_2$ |  |  |
| 2 |  | $-CH_3$ | |
| 3 |  | $-CH_2CH_3$ | |
| 4 | (cyclohexyl) | $-CH_3$ | |
| 2 | $-CH_3$ | $-CH_2CH=CHCH_3$ | |
| 3 | $-CH_3$ | $-CH_2CH_2CH=CH_2$ | |

FORMULATIONS

Useful formulations of the compounds of Formula I can be prepared in conventional ways. They include dusts, granules, pellets, solutions, emulsions, emulsifiable concentrates and the like. Many of these may be applied directly. Sprayable formulations can be extended in suitable media and used at spray volumes of from a few pints to several hundred gallons per acre. High strength compositions are primarily used as intermediates for further formulations. The formulations, broadly, contain about 1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE II

| | Active Ingredient | Weight Percent* Diluent(s) | Surfactant(s) |
|---|---|---|---|
| Oil Suspensions, Emulsions, Solutions (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength | 90–99 | 0–10 | 0–2 |

Lower or higher levels of active ingredient can, of course, be present depending on the intended use and the physical properties of the compound. For example, many of the compounds are oils or relatively low melting solids. In these cases, the strength of granules must be limited because of physical handling considerations. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey. The denser diluents are preferred for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

J. B. Buchanan, U.S. Pat. No. 3,576,834, Apr. 27, 1971, Col. 5, Lines 36 through Col. 7, Line 70 and Examples 1–4, 17, 106, 123–140;

R. R. Shaffer, U.S. Pat. No. 3,560,616, Feb. 2, 1971, Col. 3, Line 48 through Col. 7, Line 26 and Examples 3–9, 11–18;

E. Somers, "Formulation", Chapter 6 in Torgeson, "Fungicides", Vol. I, Academic Press, New York, 1967.

EXAMPLE 2

Solution

Methyl 2,2,2-trifluoro-N-[N-methyl-N-[[2-(propoxycarbonyl)phenyl]dithio]aminocarbonyloxy]

| | |
|---|---|
| ethanimidothioate | 30% |
| Dimethylformamide | 70% |

The ingredients are combined and stirred to produce a solution, which can be used for low volume applications.

EXAMPLE 3

Dust

| | |
|---|---|
| Solution of Example 2 | 5% |
| Pyrophyllite (powder) | 95% |

The solution is sprayed on the pyrophyllite diluent. The mixture is thoroughly blended and then packaged. The product is suitable for use as a dust.

EXAMPLE 4

Emulsifiable Concentrate

Methyl 2,2,2-trifluoro-N-[N-[[2-(3-methylbutoxycarbonyl)phenyl]dithio]-N-methylaminocarbonyloxy]

| | |
|---|---|
| ethanimidothioate | 30% |
| Blend of oil soluble sulfonates and polyoxyethylene ethers | 4% |
| Xylene | 66% |

The ingredients are combined and stirred with gentle warming to speed solution. A fine screen filter is included in packaging operation to insure the absence of any extraneous undissolved material in the product.

EXAMPLE 5

Granule

| | |
|---|---|
| Solution of Example 2 | 15% |
| attapulgite granules (U.S.S. 20-40 mesh; 0.8-0.42 mm) | 85% |

The solution is sprayed on the surface of the granules in a double-cone blender. The granules are dried and packaged.

EXAMPLE 6

Extruded Pellet

Methyl 2,2,2-trifluoro-N-[N-[[2-(methoxycarbonyl)phenyl]dithio]-N-methylaminocarbonyloxy]-

| | |
|---|---|
| ethanimidothioate | 25% |
| anhydrous sodium sulfate | 10% |
| crude calcium ligninsulfonate | 5% |
| sodium alkylnapthalenesulfonate | 1% |
| calcium/magnesium bentonite | 59% |

The ingredients are blended, hammer-milled and then moistened with about 12% water. The mixture is extruded as cyclinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

USE

The compounds of Formula I have insecticidal activity on major agricultural, public health and household pests.

The examples demonstrate the control efficacy of these compounds.

These compounds have a wide spectrum of insecticidal activity, controlling economically significant pest species in the orders Lepidoptera, Homoptera, Diptera and Coleoptera. More specifically, insects controlled by these compounds include, but are not limited to; the southern armyworm (*Spodoptera eridania*), beet armyworm (*Spodoptera exigua*), bean aphid (*Aphis fabae*), housefly (*Musca domestica*), boll weevil (*Anthonomus grandis*), tobacco budworm (*Heliothis virescens*), corn rootworm (*Diabrotica spp.*), and corn wireworm (*Melanotus cribulosus*).

Control is achieved through application of one or more of the compounds of Formula I to the area to be protected, to the pests themselves and/or the locus of infestation. The usual methods of application to agricultural crops, using compounds of this invention, are by foliar applications, soil applications, or applications to those plant parts which are to be protected. Applications, however, are not limited to these methods. The rate of application required for effective control is dependent upon both biological factors, e.g., the pest species, its life stage, size and location, and upon nonbiological factors, e.g., weather conditions (temperature, rainfall, humidity, etc.), the time of year, application method, crop (plant growth habit and characteristics), and agronomic factors (crop spacing, soil type, etc.). In general, application rates of 0.07 to 8 kg/ha may be required for pest control in agriculture, the rates being dependent upon the above listed biological and non-biological factors. However, rates of 0.14 to 2 kg/ha will, under normal circumstances result in effective control. Rates of 0.28 to 1.5 kg/ha will normally be used in large scale field operations.

Compounds of Formula I can be mixed with insecticides, fungicides, nematicides, bactericides, acaricides, and/or other biologically active compounds, in order to achieve effective control with a minimum of input of material, time and effort. The mixture ratio for each part by weight of compounds of this invention with the above listed biologically active chemicals may vary from 0.20 to 5.00 parts by weight. The following list consists of a few select examples of chemicals presently employed in the above listed control classes. The mixture composition, however, is not to be construed as being limited solely to the various possible combinations of those compounds.

INSECTICIDES 3-hydroxy-N-methylcrotonamide (dimethylphosphate)ester (Azodrin ®)

methylcarbamic acid, ester with 2,3-dihydro-2,2-dimethyl-7-benzofuranol (Furadan ®)

O-[2-chloro-1-(2,4,5-trichlorophenyl)vinyl]phosphoric acid, O',O'-dimethyl ester (Gardona ®)

2-mercaptosuccinic acid, diethyl ester S-ester with thionophosphoric acid, dimethyl ester (Malathion ®)

phosphorothioic acid, O,O-dimethyl, O-p-nitrophenyl ester (methyl parathion)

methylcarbamic acid, ester with α-naphthol (Sevin ®)

methyl O-(methylcarbamoyl)thiolacetohydroxamate (methomyl)

N'-(4-chloro-o-tolyl)-N,N-dimethylformamidine (Galecron ®)
O,O-diethyl-O-(2-isopropyl-4-methyl-6-pyrimidinyl-phosphorothioate (Diazinon ®).
octachlorocamphene (toxaphene)
O-ethyl O-p-nitrophenyl phenylphosphonothioate (EPN) cyano(3-phenoxyphenyl)-methyl-4-chloro-α-(1-methylethyl)benzeneacetate (Pydrin ®)
(3-phenoxyphenyl)methyl(+)-cis,trans-3-(2,2-dichloroethenyl)-2,2-dimethylcyclopropanecarboxylate (Ambush ®)
O-ethyl-S-(p-chlorophenyl)ethylphosphonodithioate (Curacron ®)
phosphorothiolothionic acid, O-ethyl-O-[4-(methylthio)phenyl]-S-n-propyl ester (Bolstar ®)

FUNGICIDES methyl 2-benzimidazolecarbamate (carbendazim)
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (Curzate ®)
N-trichloromethylthiotetrahydrophthalimide (captan)
N-trichloromethylthiophthalimide (folpet)

NEMATICIDES

S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl-O'-[4-(methylthio)-m-tolyl]diester (Nemacur ®)

BACTERICIDES tribasic copper sulfate
streptomycin sulfate

Acaricides seneciocic acid, ester with 2-sec-butyl-4,6-dinitrophenol (Morocide ®)
6-methyl-1,3-dithiolo[2,3-β]quinonolin-2-one (Morestan ®)
ethyl 4,4'-dichlorobenzilate (Chlorobenzilate ®)
1,1-bis(p-chlorophenyl)-2,2,2-trichloroethanol (Kelthane ®)
bis(pentochloro-2,4-cyclopentadien-1-yl) (Pentac ®)
tricyclohexyl trihydroxide (Plictran ®)

EXAMPLE I

The foliage only of red kidney bean plants in the two-leaf stage was sprayed to run-off with a dispersion of the compounds named below at 0.01% concentration. Dispersions were prepared by dissolving appropriately weighed quantities of the active ingredient in 10 ml of acetone and diluting to 100 ml with water containing a surface active agent (Duponol L-144 WDG) at 1:3000. After drying, leaves were excised and placed in covered 10 cm petri dishes along with moist filter paper to keep them fresh. Ten southern armyworm larvae were placed in each dish. Tests were run in duplicate. The units were kept in a room maintained at 25°±2° C., 53±5% RH. Results were recorded at the end of 2 days.

| Compound | % A.I. Spray Concentration | % Mortality (2 days) |
|---|---|---|
| Methyl 2,2,2-trifluoro-N-[N-[[2-(ethoxycarbonyl)-phenyl]dithio]-N-methyl-aminocarbonyloxy]ethanimidothioate | .01 | 100 |
| Methyl 2,2,2-trifluoro-N-[N-[[2-(butoxycarbonyl)phenyl]-dithio]-N-methylaminecarbonyloxy]ethanimidothioate | 0.1 | 100 |

EXAMPLE II

The test units used to demonstrate aphicidal effectiveness through foliar application consisted of two excised nasturtium leaves contained in a 2-ounce narrow mouthed bottle. The bottle contained water for the plant tissue, and cotton was packed around the stems in the neck of the bottle to prevent the spray solution from contacting the water. The two leaves supported approximately 80 aphids in various stages of growth. The test units were sprayed to run off with a 0.05% concentration of the compounds made up in aqueous solution containing 1:3000 parts of Duponol surfactant. Results were observed 1 day after application and are set forth below.

| Compound | % A.I. Spray Concentration | % Control |
|---|---|---|
| Methyl 2,2,2-trifluoro-N-[N-[[2-(butoxycarbonyl)phenyl]-dithio]-N-methylaminocarbonyloxy]ethanimidothioate | .05 | 100 |
| Methyl 2,2,2-trifluoro-N-[N-[[2-(methoxycarbonyl)phenyl]-dithio]-N-methylaminocarbonyloxy]ethanimidothioate | .05 | 100 |
| Methyl 2,2,2-trifluoro-N-[N-[[2-(1-methylethoxycarbonyl)phenyl]dithio]-N-methyl-aminocarbonyloxy]ethanimidothioate | .05 | 100 |
| Methyl 2,2,2-trifluoro-N-[N-[[2-(3-methylbutoxycarbonyl)phenyl]dithio]-N-methyl-aminocarbonyloxy]ethanimidothioate | .05 | 100 |

EXAMPLE III

Tobacco budworm, *Heliothis virescens*, larvae were treated topically with the compound named below. One microliter of this concentration (10 μg/larva) was applied to the dorso-prothoracic area of each larva tested. The stock solution was prepared by dissolving an appropriately weighed quantity of active ingredient in a predetermined quantity of acetone. Further diluting with acetone yielded the desired concentration. Larvae were treated in the individual 1-oz. cups in which they were reared on artificial diet. Fifteen larvae were treated with the desired concentration and kept in a growth room at 26°±0.5° C. and 50-60% RH. Mortality readings were taken at 72 hours.

| Compound | μg/larva | % Mortality |
|---|---|---|
| Methyl 2,2,2-trifluoro-N-[N-methyl-N-[[2-(propoxycarbonyl)phenyl]dithio]- | | |

| Compound | μg/larva | % Mortality |
|---|---|---|
| aminocarbonyloxy]ethanimidothioate | .01 | 93 |

EXAMPLE IV

Twenty-five house fly adults are secured in screened stainless steel ring cages and treated with acetone dispersions of compounds of this invention at 0.05% concentration. The stock dispersion is prepared by dissolving an appropriately weighed quantity of active ingredient in a predetermined quantity of acetone. Further diluting with acetone yields the desired concentration. After treating, the units are kept in a room maintained at 25°±2° C., 50% RH. Results are recorded at the end of 1 day.

| Compound | % A.I. Spray Concentration | % Mortality |
|---|---|---|
| Methyl 2,2,2-trifluoro-N-[N-[[2-(butoxycarbonyl)phenyl]dithio]-N-methylaminocarbonyloxy]ethanimidothioate | .05 | 100 |
| Methyl 2,2,2-trifluoro-N-[N-[[2-(methoxycarbonyl)phenyl]dithio]-N-methylaminocarbonyloxy]ethanimidothioate | .05 | 100 |
| Methyl 2,2,2-trifluoro-N-[N-[[2-(1-methylethoxycarbonyl)phenyl]dithio]-N-methylaminocarbonyloxy]ethanimidothioate | .05 | 100 |
| Methyl 2,2,2-trifluoro-N-[N-[[2-(3-methylbutoxycarbonyl)phenyl]dithio]-N-methylaminocarbonyloxy]ethanimidothioate | .05 | 100 |

EXAMPLE V

A grain of corn was placed on Michigan peat in each of a series of cups (2 inches×2 inches). The cups were sprayed with a 0.05% acetone solution of the indicated compounds. The grains were then covered with more peat, and each cup was infested with 10 larvae of the southern corn rootworm. Percent rootworm control was determined five days later as follows: 0% control=no plant growth; 100% control=plant growth comparable to that in an uninfested cup.

| Compound | Percent Control |
|---|---|
| Methyl 2,2,2-trifluoro-N-[N-[[2-(butoxycarbonyl)phenyl]dithio-N-methylaminocarbonyloxy]ethanimidothioate | 100 |

EXAMPLE VI

A grain of corn was placed on Michigan peat in each of a series of cups (2 inches×2 inches). The cups were sprayed with 0.025% concentration of the indicated compounds. The grains were then covered with more peat, and each cup was infested with 10 larvae of the southern corn rootworm. Percent rootworm control was determined five days later as follows: 0% control=no plant growth; 100% control=plant growth comparable to that in an uninfested cup.

| Compound | % A.I. Spray Concentration | % Mortality |
|---|---|---|
| Methyl 2,2,2-trifluoro-N-[N-[[2-(methoxycarbonyl)phenyl]dithio]-N-methylaminocarbonyloxy]ethanimidothioate | .025 | 100 |
| Methyl 2,2,2-trifluoro-N-[N-[[2-(1-methylethoxycarbonyl)phenyl]dithio]-N-methylaminocarbonyloxy]ethanimidothioate | .025 | 100 |
| Methyl 2,2,2-trifluoro-N-[N-methyl-N-[[2-propoxycarbonyl)phenyl]dithio]aminocarbonyloxy]ethanimidothioate | .025 | 100 |

What is claimed is:
1. A compound of the formula:

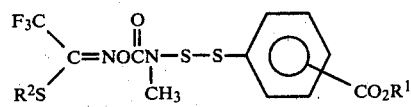

wherein
$R^2$ is $C_1$-$C_4$ alkyl, $C_3$-$C_4$ alkenyl, or benzyl;
$R_1$ is $C_1$-$C_{20}$ alkyl or $C_5$-$C_8$ cycloalkyl.
2. A compound of claim 1 wherein $R^2$ is $CH_3$.
3. A compound of claim 2 wherein the $CO_2R^1$ group is in the ortho position.
4. A compound of claim 1 wherein $R^1$ is $C_1$-$C_8$ alkyl.
5. A compound of claim 2 wherein $R^1$ is $C_1$-$C_8$ alkyl.
6. A compound of claim 3 wherein $R^1$ is $C_1$-$C_8$ alkyl.
7. The compound of claim 1 which is methyl 2,2,2-trifluoro-N-[N-methyl-N-[[2-(propoxycarbonyl)phenyl]dithio]aminocarbonyloxy]ethanimidothioate.
8. The compound of claim 1 which is methyl 2,2,2-trifluoro-N-[N-[[2-(3-methylbutoxycarbonyl)phenyl]dithio]-N-methylaminocarbonyloxy]ethanimidothioate.
9. The compound of claim 1 which is methyl 2,2,2-trifluoro-N-[N-[[2-(methoxycarbonyl)phenyl]dithio]-N-methylaminocarbonyloxy]ethanimidothioate.
10. The compound of claim 1 which is methyl 2,2,2-trifluoro-N-[N-[[2-(1-methylethoxycarbonyl)phenyl]dithio]-N-methylaminocarbonyloxy]ethanimidothioate.
11. The compound of claim 1 which is methyl 2,2,2-trifluoro-N-[N-[[2-(ethoxycarbonyl)phenyl]dithio]-N-methylaminocarbonyloxy]ethanimidothioate.
12. The compound of claim 1 which is methyl 2,2,2-trifluoro-N-[N-[[2-(butoxycarbonyl)phenyl]dithio]-N-methylaminocarbonyloxy]ethanimidothioate.
13. A process for forming a compound of claim 1 which comprises contacting:

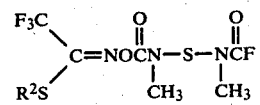

and

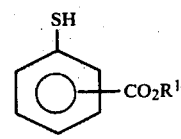

wherein
$R^1$ and $R^2$ are as previously defined.

14. An insecticidal composition consisting essentially of a surfactant, diluent or mixtures thereof and an insecticidally effective amount of a compound of claim 1.

15. An insecticidal composition consisting essentially of a surfactant, diluent or mixtures thereof and an effective amount of a compound of claim 2.

16. An insecticidal composition consisting essentially of a surfactant, diluent or mixtures thereof and an effective amount of a compound of claim 3.

17. An insecticidal composition consisting essentially of a surfactant, diluent or mixtures thereof and an effective amount of a compound of claim 4.

18. An insecticidal composition consisting essentially of a surfactant, diluent or mixtures thereof and an effective amount of a compound of claim 5.

19. An insecticidal composition consisting essentially of a surfactant, diluent or mixtures thereof and an effective amount of a compound of claim 6.

20. An insecticidal composition consisting essentially of a surfactant, diluent or mixtures thereof and an effective amount of the compound of claim 7.

21. An insecticidal composition consisting essentially of a surfactant, diluent or mixtures thereof and an effective amount of the compound of claim 8.

22. An insecticidal composition consisting essentially of a surfactant, diluent or mixtures thereof and an effective amount of the compound of claim 9.

23. An insecticidal composition consisting essentially of a surfactant, diluent or mixtures thereof and an effective amount of the compound of claim 10.

24. An insecticidal composition consisting essentially of a surfactant, diluent or mixtures thereof and an effective amount of the compound of claim 11.

25. An insecticidal composition consisting essentially of a surfactant, diluent or mixtures thereof and an effective amount of the compound of claim 12.

26. A method of controlling insects which comprises applying to a locus to be protected an insecticidally effective amount of a compound of claim 1.

27. A method of controlling insects which comprises applying to a locus to be protected an insecticidally effective amount of a compound of claim 2.

28. A method of controlling insects which comprises applying to a locus to be protected an insecticidally effective amount of a compound of claim 3.

29. A method of controlling insects which comprises applying to a locus to be protected an insecticidally effective amount of a compound of claim 4.

30. A method of controlling insects which comprises applying to a locus to be protected an insecticidally effective amount of a compound of claim 5.

31. A method of controlling insects which comprises applying to a locus to be protected an insecticidally effective amount of the compound of claim 6.

32. A method of controlling insects which comprises applying to a locus to be protected an insecticidally effective amount of the compound of claim 7.

33. A method of controlling insects which comprises applying to a locus to be protected an insecticidally effective amount of the compound of claim 8.

34. A method of controlling insects which comprises applying to a locus to be protected an insecticidally effective amount of the compound of claim 9.

35. A method of controlling insects which comprises applying to a locus to be protected an insecticidally effective amount of the compound of claim 10.

36. A method of controlling insects which comprises applying to a locus to be protected an insecticidally effective amount of the compound of claim 11.

37. A method of controlling insects which comprises applying to a locus to be protected an insecticidally effective amount of the compound of claim 12.

* * * * *